(12) United States Patent
Gomez et al.

(10) Patent No.: US 11,730,940 B2
(45) Date of Patent: Aug. 22, 2023

(54) SYSTEM, METHOD AND APPARATUS FOR PROVIDING MULTIPLE FUNCTIONS IN A SURGICAL PROCEDURE

(71) Applicants: Ricardo Alexander Gomez, Lighthouse Point, FL (US); Sandy Lawrence Heck, Los Angeles, CA (US); Eric William Conley, South Berwick, ME (US)

(72) Inventors: Ricardo Alexander Gomez, Lighthouse Point, FL (US); Sandy Lawrence Heck, Los Angeles, CA (US); Eric William Conley, South Berwick, ME (US)

(73) Assignee: NEW WAVE ENDO-SURGICAL CORP., Coconut Creek, FL (US)

( * ) Notice: Subject to any disclaimer, the term of this patent is extended or adjusted under 35 U.S.C. 154(b) by 193 days.

(21) Appl. No.: 15/613,648

(22) Filed: Jun. 5, 2017

(65) Prior Publication Data

US 2018/0221562 A1 Aug. 9, 2018

Related U.S. Application Data

(60) Provisional application No. 62/455,667, filed on Feb. 7, 2017.

(51) Int. Cl.
*A61B 18/14* (2006.01)
*A61M 39/02* (2006.01)
(Continued)

(52) U.S. Cl.
CPC ..... *A61M 39/0247* (2013.01); *A61B 18/1482* (2013.01); *A61F 7/12* (2013.01);
(Continued)

(58) Field of Classification Search
CPC ..... A61B 18/1482; A61B 2017/22072–22077; A61B 2018/00196; A61M 39/0247
See application file for complete search history.

(56) References Cited

U.S. PATENT DOCUMENTS 5,254,117 A * 10/1993 Rigby ............... A61B 18/1482
606/42
5,350,356 A * 9/1994 Bales ................. A61M 3/0233
604/27
(Continued)

FOREIGN PATENT DOCUMENTS

WO 9622056 7/1996

OTHER PUBLICATIONS

International Search Report for PCT/US18/16942 dated Mar. 31, 2018.

*Primary Examiner* — Linda C Dvorak
*Assistant Examiner* — Ryan T Clark
(74) *Attorney, Agent, or Firm* — Grogan, Tuccillo & Vanderleeden, LLP

(57) ABSTRACT

A surgical instrument includes an instrument shaft having a proximal end and a distal end, and an interior passageway extending from the proximal end to the distal end, a first conduit fluidly coupled to the instrument shaft and being configured for selective connection to an irrigation source, and a second conduit fluidly coupled to the instrument shaft and being configured for selective connection to a vacuum source, wherein the instrument shaft is configured for percutaneous insertion without use of a trocar.

18 Claims, 13 Drawing Sheets

(51) Int. Cl.
    *A61F 7/12*      (2006.01)
    *A61B 18/00*     (2006.01)
    *A61B 17/00*     (2006.01)
    *A61B 17/32*     (2006.01)

(52) U.S. Cl.
    CPC ............... *A61B 2017/00353* (2013.01); *A61B 2017/00393* (2013.01); *A61B 2017/320044* (2013.01); *A61B 2018/00595* (2013.01); *A61B 2217/005* (2013.01); *A61B 2217/007* (2013.01); *A61B 2218/002* (2013.01); *A61B 2218/008* (2013.01)

(56) References Cited

U.S. PATENT DOCUMENTS

| | | | |
|---|---|---|---|
| 5,451,222 A | 9/1995 | De Maagd et al. | |
| 5,830,214 A * | 11/1998 | Flom | A61B 18/1482 606/41 |
| 5,910,104 A * | 6/1999 | Dobak, III | A61B 18/02 600/121 |
| 6,063,085 A | 5/2000 | Tay et al. | |
| 6,086,583 A * | 7/2000 | Ouchi | A61B 1/00089 604/35 |
| 9,138,207 B2 * | 9/2015 | Igov | A61B 17/00234 |
| 2002/0095152 A1 * | 7/2002 | Ciarrocca | A61B 18/1492 606/50 |
| 2002/0123722 A1 * | 9/2002 | French | A61M 1/0064 604/118 |
| 2010/0094143 A1 * | 4/2010 | Mahapatra | A61B 5/4887 600/486 |
| 2011/0230853 A1 | 9/2011 | Ihde, II | |
| 2013/0267938 A1 * | 10/2013 | Greenberg | A61B 18/24 606/15 |
| 2015/0216620 A1 * | 8/2015 | Davies | A61B 90/39 606/41 |
| 2016/0022367 A1 * | 1/2016 | Brody | A61B 90/70 134/6 |
| 2016/0051408 A1 | 2/2016 | Baerveldt et al. | |
| 2017/0325886 A1 * | 11/2017 | Graham | A61B 18/1206 |

* cited by examiner

SYSTEM, METHOD AND APPARATUS FOR PROVIDING MULTIPLE FUNCTIONS IN A SURGICAL PROCEDURE

CROSS-REFERENCE TO RELATED APPLICATIONS

This application claims the benefit of U.S. Provisional Application Ser. No. 62/455,667, filed on Feb. 7, 2017, entitled Multifunctional Needlescopic Peanut, which is hereby incorporated by reference herein in its entirety.

FIELD OF THE INVENTION

The present invention relates generally to medical instruments for use in laparoscopic surgery and, more particularly, to a multi-function instrument for providing at least suction and irrigation in a laparoscopic surgery.

BACKGROUND OF THE INVENTION

Today, laparoscopic surgery is the preferred method for performing surgery. It typically consists of creating small openings to the abdomen of a patient for the introduction of trocars and laparoscopic instruments. For example, prior to starting a surgical procedure, a small incision is created allowing a trocar device to be inserted through the umbilicus. Additional percutaneous incisions are made, typically between 5-15 mm, for inserting additional trocars. The trocars typically range in diameter between 5 to 12 mm and provide a passageway for the introduction of medical devices into the abdomen. That is, the trocars provide access points for surgery. Insufflators are then used to pump gases into the abdomen cavity, creating the space necessary for surgeons to manipulate their tools and perform medical procedures, as well as to provide a viewing field within the abdomen.

During certain medical procedures, it may be desirable to remove body tissues. Removal and tearing of tissue is referred to as dissection, and a tool that is often used for this purpose is referred to as dissector. Dissection, as in the context of laparoscopic surgery, can be described in two general forms, blunt dissection or sharp dissection. Blunt dissection is defined as a technique in surgery or anatomical dissection whereby tissue planes are separated or opened and underlying structures are exposed without cutting. The advantages of using blunt dissection are the preservation of the local regional architecture and structural integrity of nerves, vessels, and lymph nodes without cutting many of the tissues being dissected that contain the blood vessels, nerves, and lymph vessels. Conversely, sharp dissection involves gaining access to tissues by incising or cutting with a sharp instrument. The disadvantage to this approach as it relates to laparoscopic surgery is that bleeding occurs which must be stopped, requiring another procedure with the possibilities of complications and longer recovery times.

In connection with the above, during a typical laparoscopic surgery, a surgeon uses a device called a laparoscope to visually inspect what takes place inside the patient's abdominal cavity. Tactile ability to touch and feel body tissues is lost. In an effort to compensate for these disadvantages, a dissector is often used to move or separate body tissues with minimal bleeding. The problems associated with existing dissectors, however, are that they often have small sized heads, absorb very small amounts of fluid, are uniform in the material they use and lack the functionality of irrigation and suction. Accordingly, a separate irrigator and/or aspirator is often used to add or remove fluids and debris. Each of these instruments typically occupies a trocar, reducing the surgeon's ability to insert other instruments and potentially requiring additional incisions and the cost of additional trocars.

It is therefore an object of this invention to minimize the need to use multiple, distinct tools during dissection. In particular, there is a need in the field for a multifunction instrument for use in laparoscopic surgeries that has a large head that improves manipulation, is able to absorb large amounts of fluids, uses a combination of materials at the head to perform different tasks, and has the ability to provide the functions of both irrigation and suction.

SUMMARY OF THE INVENTION

It is an object of the present invention to provide a multifunctional instrument for use in laparoscopic surgeries.

It is another object of the present invention to provide a multifunctional instrument for use in laparoscopic surgeries that minimizes and/or reduces the number of trocars, and thus incisions, necessary to perform a required set of surgical procedures.

It is another object of the present invention to provide a multifunctional instrument that is capable of suction/irrigation, blunt dissection, smoke evacuation, electrocautery, lens cleaning or some subset of these functions.

These and other objects are achieved by the present invention.

According to an embodiment of the present invention, a surgical instrument includes an instrument shaft having a proximal end and a distal end, and an interior passageway extending from the proximal end to the distal end, a first conduit fluidly coupled to the instrument shaft and being configured for selective connection to an irrigation source, and a second conduit fluidly coupled to the instrument shaft and being configured for selective connection to a vacuum source, wherein the instrument shaft is configured for percutaneous insertion without use of a trocar.

According to another embodiment of the present invention, a method of performing a surgical procedure is provided. The method includes the steps of piercing the skin of a patient with a piercing shaft slidably received within a hollow shaft of a multifunctional instrument, advancing the shaft of the multifunctional instrument into the body of the patient to a target location, removing the piercing shaft from the hollow shaft of the multifunctional instrument, introducing an instrument head into the body of the patient through a trocar, and attaching a distal end of the hollow shaft to the instrument head within the body of the patient.

In yet another embodiment of the present invention, an instrument head for a multifunction surgical instrument is provided. The instrument head includes a body having a proximal end and a distal end, and an inner cannula tube defining an interior passageway through the body, an attachment means adjacent to the proximal end for removably connecting the instrument head to an instrument shaft of a multifunctional instrument, an opening at the distal end in fluid communication with the interior passageway, and a cauterizing tip located on the distal end of the instrument head adjacent to the opening. The attachment means is configured to establish a conductive pathway from the instrument shaft to the cauterizing tip when the instrument head is connected to the instrument shaft to enable cauterization of body tissue during a surgical operation. The inner cannula tube defining the interior passageway enables both vacuum suction and irrigation during the surgical procedure.

The outer diameter of the instrument head is substantially greater than an outer diameter of the instrument shaft such that the instrument shaft can be inserted into the body of a patient without the use of a trocar, for subsequent attachment of the instrument head to the instrument shaft within the body.

In yet another embodiment, a method of performing a surgical procedure under continuous direct visualization is provided. The method includes the steps of, piercing the skin of a patient with a piercing shaft slidably received within a hollow shaft of a multifunctional instrument, advancing the shaft of the multifunctional instrument into the body of the patient to a target location, without use of a trocar, removing the piercing shaft from the hollow shaft of the multifunctional instrument, introducing an instrument head into the body of the patient through a trocar, and under continuous direct visualization, attaching a distal end of the hollow shaft to the instrument head within the body of the patient.

BRIEF DESCRIPTION OF THE DRAWING

The present invention will be better understood from reading the following description of non-limiting embodiments, with reference to the attached drawings, wherein below.

DETAILED DESCRIPTION OF THE PREFERRED EMBODIMENT

Figure 1:
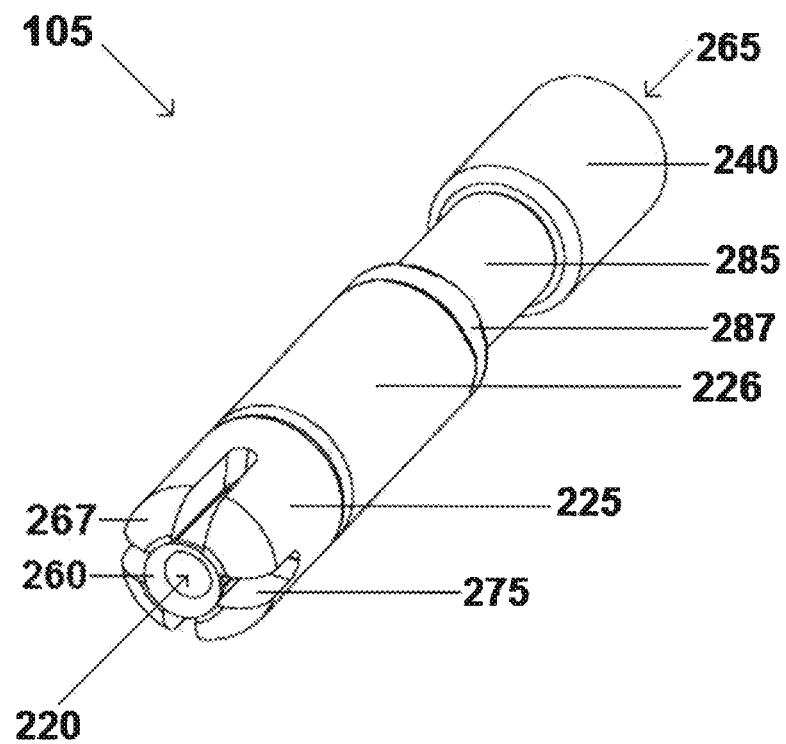
FIG. 1 is a perspective view of an instrument head of a multifunctional instrument, according to an embodiment of the present invention.

With reference to FIGS. 1-4B, an instrument head 105 for use with a multifunctional instrument according to an embodiment of the present invention is illustrated. As shown therein, the instrument head 105 is generally cylindrical in shape and includes a proximal end 265 having an attachment housing 240, and a distal end having a rounded tip 267 having an opening 220. The housing 240 is generally cylindrical in shape and encloses an attachment means for attaching the instrument head 105 to an instrument shaft, as discussed in detail hereinafter. As also discussed hereinafter, the opening 220 in the distal end of the instrument head allows for vacuum suctioning, irrigation, the introduction of liquids, and the introduction of thin medical devices such as, for example, a piercing needle or a cautery spatula tip 345, during various surgical processes.

The instrument head 105 may further include a generally cylindrical cleaning portion 285 adjacent to the attachment housing 240. The cleaning portion 285 includes a cleaning surface on an outer periphery thereof for cleaning a laparoscope lens. For example, in an embodiment, the cleaning portion 285 may be formed from or otherwise include an absorbent material such as, for example, a gauze material, microfiber, cotton, polyester or foam. In certain embodiments, a plastic may also be utilized. Preferably, the cleaning surface of the cleaning portion 285 includes a surfactant or other liquid that facilitates cleaning of a lens. In an embodiment, the cleaning portion 285 may include an embedded opaque x-ray-detectable strip, ensuring that no components or foreign objects are left behind in the abdominal cavity of the patient. As illustrated in FIG. 1, in an embodiment, the cleaning portion 285 may have an outside diameter that is less than the outside diameter of the attachment housing 240, for the purpose of fully covering the laparoscopic lens during cleaning. In use, a surgeon can rub the laparoscopic lens along the cleaning portion 285 to quickly clean the lens and improve visual quality. A separation ring 287 may be provided to help prevent the cleaning portion 285 from slipping off of the instrument head 105, as well as to provide a degree of separation from different surface materials covering portions of the instrument head 105 to the proximal side and distal side of the separation ring 287, respectively.

As further illustrated in FIG. 1, the instrument head 105 may include a generally cylindrical frame 225 extending from the cleaning portion 285 to the rounded tip 267. The cylindrical frame 225 preferably has an outer diameter that is generally equivalent to the outer diameter of the attachment housing 240. At least a portion of the cylindrical frame 225, such as an area intermediate the cleaning portion 285 and the rounded tip 267, may be covered by a covering material 226 such as, for example, a gauze, microfiber or other standard medical industry materials such as cotton, polyester or foam. In an embodiment, the cylindrical frame 225 adjacent the rounded tip 267 and the cylindrical frame 225 adjacent to the cleaning portion 285 may be two separate components. The frame 225 may be formed from hard plastic, rubberized material, gauze wrap, or a combination of both rubber and plastic, although other materials known in the art may also be utilized without departing from the broader aspects of the present invention. Likewise, the rounded tip 267 may be formed from hard plastic, rubberized material, gauze wrap, or a combination of both rubber and plastic, although other materials known in the art may also be utilized without departing from the broader aspects of the present invention. The covering material 226 may be attached to the frame 225 and/or rounded tip by adhesive or other means known in the art. Importantly, the frame 225 helps to shape the covering material 226 applied thereto.

With further reference to FIG. 1, the rounded tip 267 at the distal end of the instrument head 105 may be formed with a plurality of longitudinal slots 275 that provide passageways from the exterior of the instrument head 105 to an interior passageway (a cannula tube) that extends from the opening 220 to the proximal end 265. These slots 275 help to prevent clogging, facilitate draining, and provide a larger vacuum path for suctioning and the like. Importantly, the rounded tip 267 of the instrument head 105 provides superior contact with bodily tissues and, as alluded to above, may be covered with a covering material that provides both absorption and friction for improved tissue dissection, as discussed hereinafter. This covering material on the rounded tip 267 may also, when wet, provides a guide path for liquids that come into contact with the wet surface area. As also shown in FIG. 1, the distal end of the instrument head 105 may include a cauterizing tip or ring generally surrounding the opening 220, the purpose of which will be discussed hereinafter.

Figure 2:
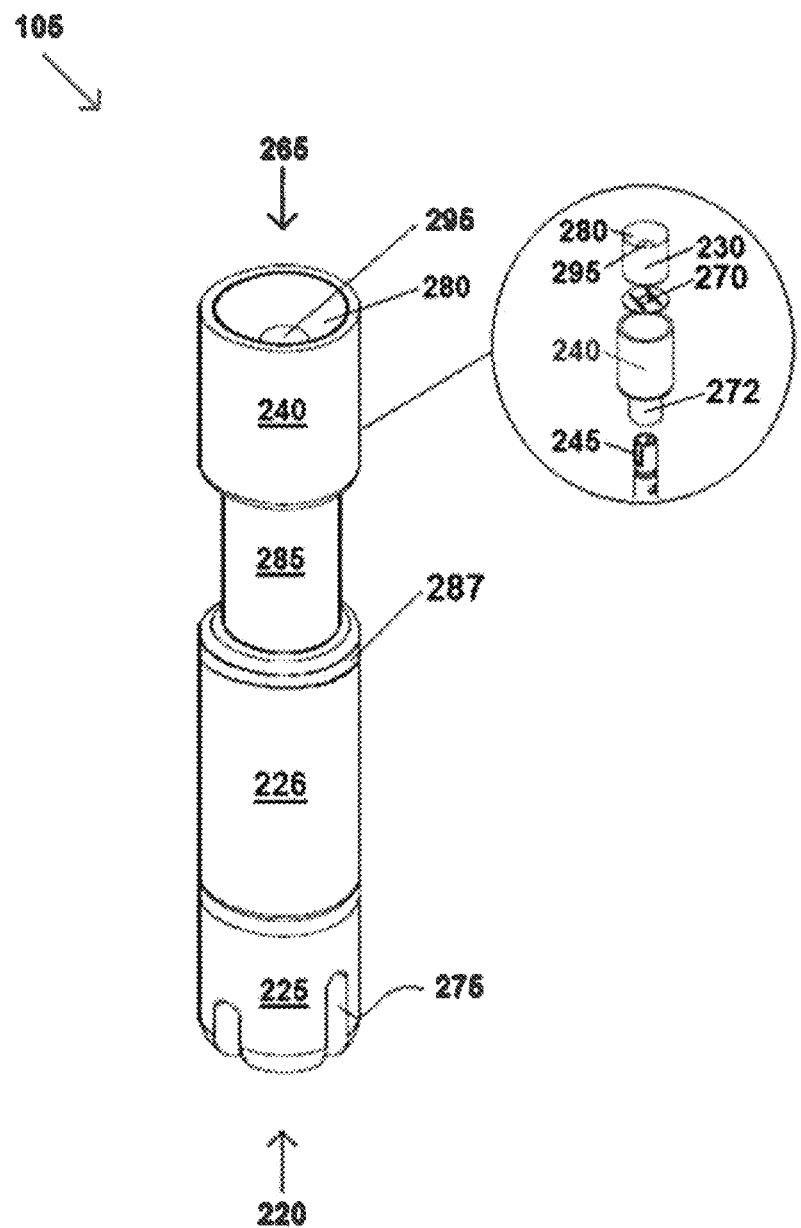
FIG. 2 is an enlarged, exploded view of the instrument head of FIG. 1, showing components housed in an attachment means.
Figure 3A:
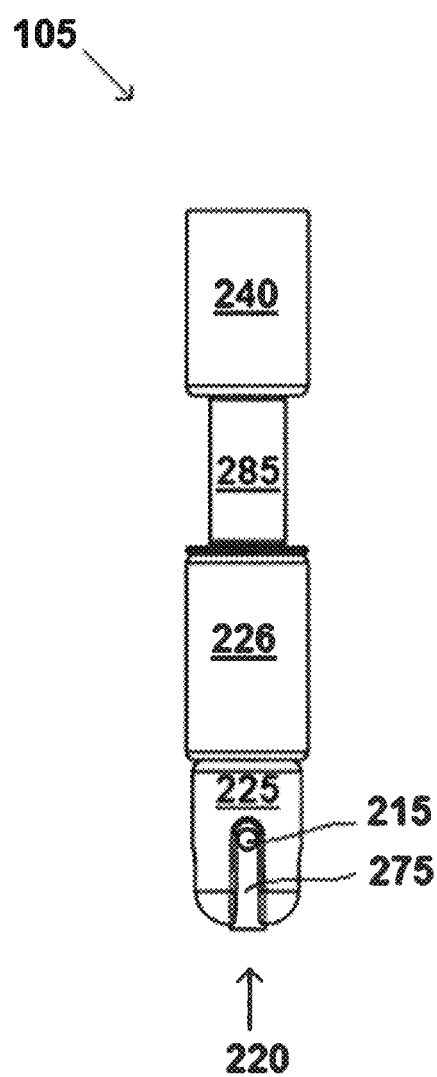
FIG. 3A is a side elevational view of the instrument head of FIG. 1.
Figure 3B:
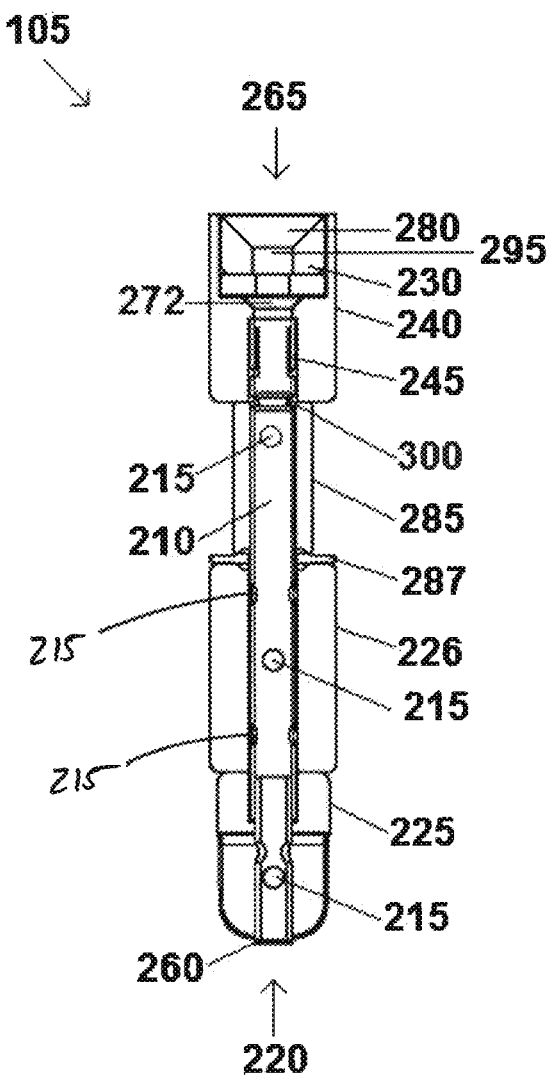
FIG. 3B is a partial cross-sectional view of the instrument head of FIG. 1.

Turning now to FIGS. 2, 3A and 3B a detailed view of the proximal end 265 and attachment housing 240 of the instrument head 105 is shown. As shown therein, the attachment housing 240 includes a passageway 295 for an instrument shaft that helps guide the instrument shaft, when inserted into the attachment housing 240, to its mating point inside the attachment housing 240. In an embodiment, the proximal end 265 of the instrument head may include a conical surface 280 surrounding the passageway 295 for facilitating and guiding the insertion of the instrument shaft into the passageway 295. The attachment housing 240 may include an attachment means positioned therein for attaching the instrument head 105 to an instrument shaft. As illustrated in FIG. 2, the attachment means include an H-clip 270 or other locking mechanism used for securely attaching the instrument head 105 to the instrument shaft. Although the attachment means is shown located in the proximal end of the instrument head 105, it is contemplated that the attachment means may be located adjacent to the distal end of the instrument head 105 or at any point therebetween. A retainer 230 may be included within the attachment housing 240 for holding the H-clip 270 or other locking mechanism in place. A small area 272 below the attachment housing 240 may be included to provide space for the leaves of the H-clip 270 to expand and firmly hold in place the instrument shaft.

As further shown in FIGS. 2, 3A and 3B an electric contact clip 245 positioned within or adjacent to the attachment housing 240 is utilized to provide an electrical pathway from the instrument shaft coupled therewith to a cannula tube 210 that extends through the instrument head 105 to the cauterizing tip 260. Importantly, when an instrument shaft is attached to the instrument head 105, an electrical pathway is established between the instrument shaft and the cauterizing tip 260, thereby enabling the instrument head 105 to be utilized to cauterize bodily tissues. In this respect, the cannula tube 210 actually serves dual purposes: (1) providing a pathway for the suctioning of fluids and debris from within the body, or for delivering fluids to a surgical site within the body, and (2) establishing an electrical pathway from the instrument shaft to the cauterizing tip 260 for cauterizing body tissues.

Figure 4A:
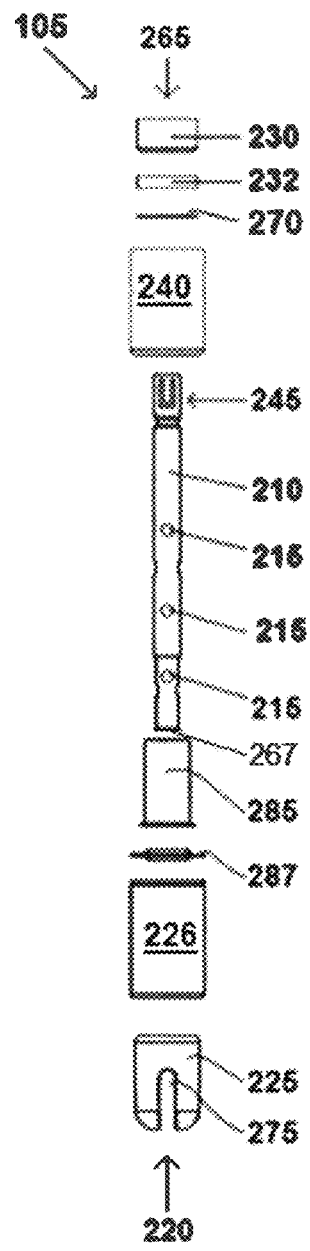
FIG. 4A is an exploded, side elevational view of the instrument head of FIG. 1.
Figure 4B:
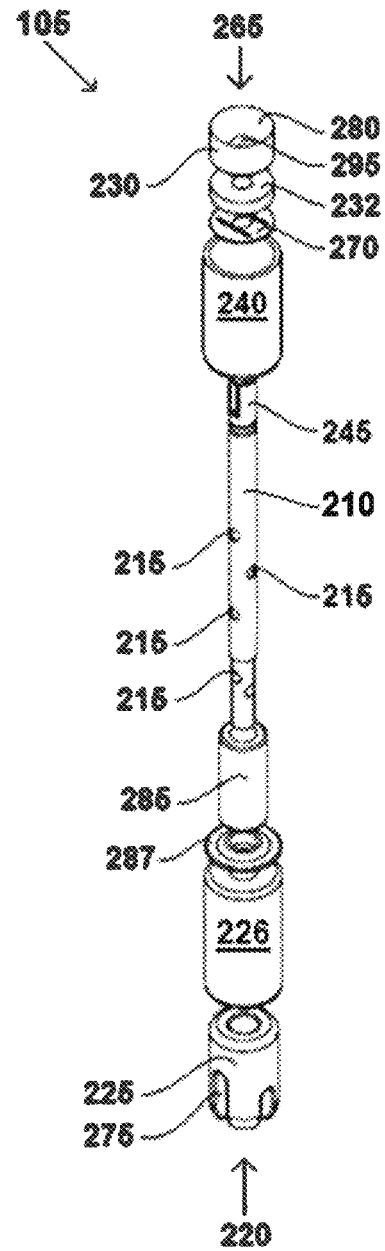
FIG. 4B is an exploded, perspective view of the instrument head of FIG. 1.

Referring specifically to FIGS. 3A-4B, in an embodiment, the cannula tube 210 may be formed with one or more orifices 215 along its longitudinal extent. For example, as illustrated in FIG. 3A, at least one of the orifices 215 may be aligned with the longitudinal slots 275, which provide a larger/wider path for liquids to be suctioned into the orifices 215 to facilitate irrigation and suction. As shown in FIGS. 3B and 4B, the orifices 215 may be staggered along the longitudinal extent of the cannula tube 210, at various peripheral locations on the cannula tube 210, to provide for improved suctioning and irrigation regardless of instrument head orientation. For example, one or more orifices 215 may be located in the area of the cleaning portion 285. In an embodiment, a rubber seal 232 may be incorporated into the instrument head 105 to provide a seal between the instrument shaft and the cannula tube 210, which may be useful during irrigation and evacuation of liquids, as best shown in FIGS. 4A and 4B.

Turning now to FIGS. 5-9, a multifunctional instrument 100 according to an embodiment of the present invention is illustrated. The multifunctional instrument 100 includes an instrument shaft 112 and an instrument head, such as instrument head 105, removably attached to a threaded, distal end 342 of the instrument shaft 112. The multifunctional instrument 100 further includes a body 322 having a handle 320, and having a multi-port connector 350 arranged at one end thereof, to which the instrument shaft 112 may be removably attached. The connector port 350 is, within the body 322, fluidly connected to an irrigation tube 317, a vacuum tube 312, and an injection port 305. A cauterizing cable 325 extends from the body 322 and is connected to likewise electrically coupled to the connector port 350 to establish an electrical connection with the instrument shaft 112, when attached to the connector port 350, as discussed hereinafter.

Figure 5:
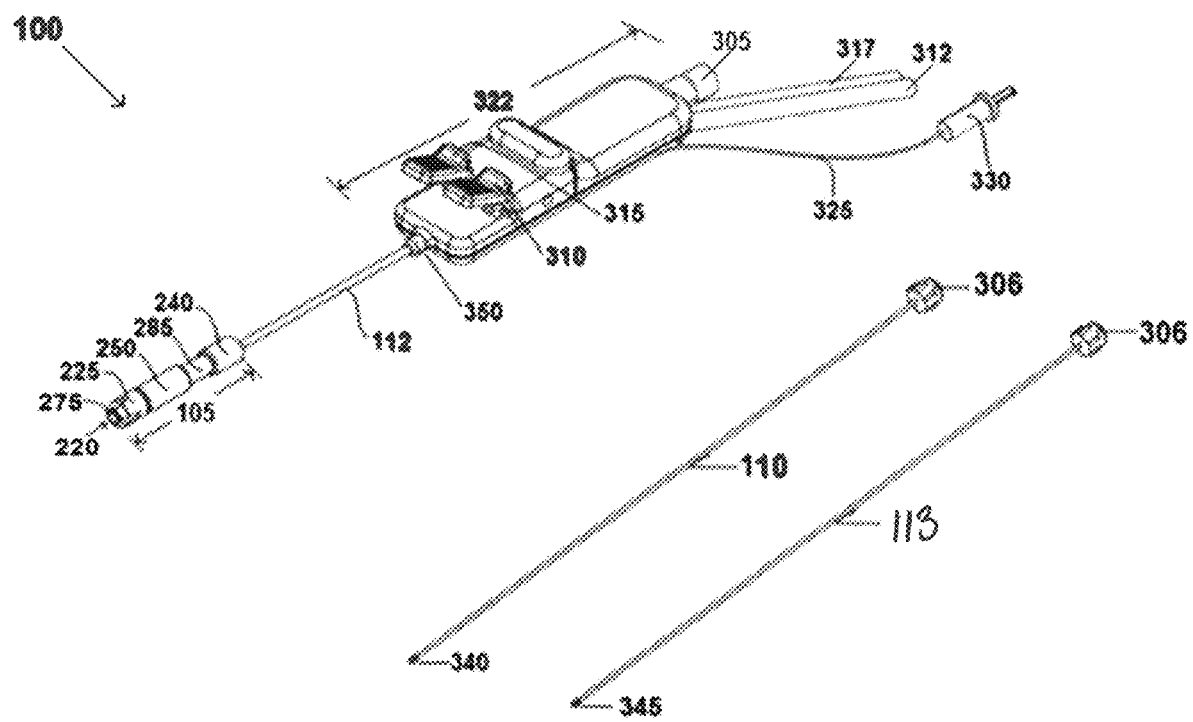
FIG. 5 is a perspective view of a multifunctional instrument having the instrument head of FIG. 1.

The vacuum tube 312 is configured for connection to a suctioning device (not shown), and the body 322 includes a suction actuating button 310 that can be utilized to selectively initiate suction whereby fluids and other debris are sucked through the orifices 215 in the instrument head 105, through the cannula tube 210, through the hollow instrument shaft 112, and to a collection reservoir. Similarly, the irrigation tube 317 is configured for connection to a liquid supply (not shown), and the instrument body 322 includes a button 315 that can be utilized to selectively execute an irrigation process whereby liquids, such as water, can be pumped or otherwise passed from the liquid supply, through the irrigation tube 317, through the instrument shaft 112, and out of one or more of the orifices 215 or opening 220 in the distal end of the instrument head 105. As also shown in FIG. 5, the cauterizing cable 325 includes a connector plug 330 that enables connection of the multifunctional instrument 100 to a power source (not shown). The cauterizing cable 325 is used for providing an electrical passage of current through the instrument shaft 112, through the cannula tube 210 in the instrument head 105, to the distal cauterizing tip 260.

Figure 9:
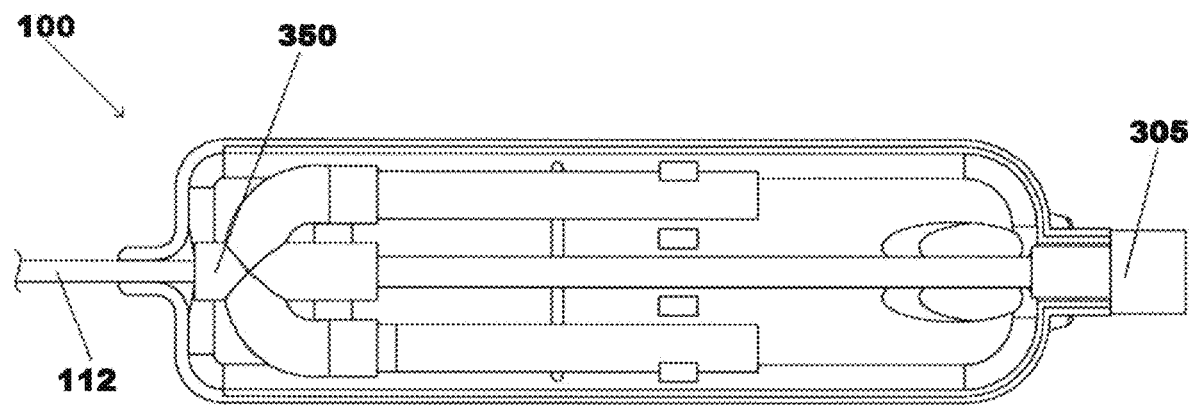
FIG. 9 is a top, cross-sectional view of a handle section of the multifunctional instrument of FIG. 5.

As additionally shown in FIG. 5, the body 322 may also include the injection port 305 that is fluidly connected to the connector port 350 through a tube or conduit that extends through the instrument body 322 (see FIG. 9). The injection port 305 allows for the injection of a medical solution or other liquid utilizing, for example, a syringe.

Figure 6:
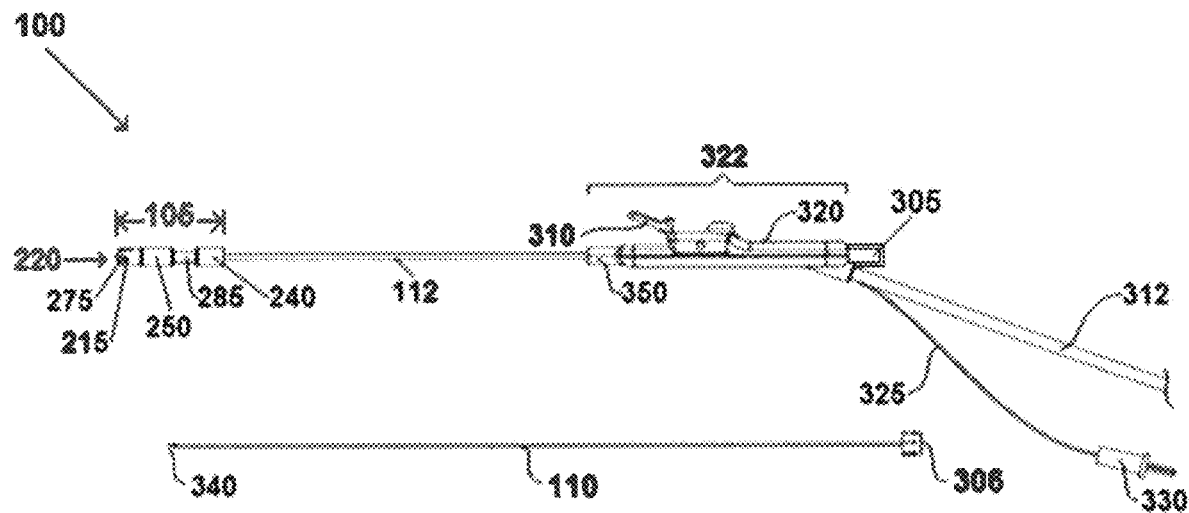
FIG. 6 is a side perspective view of the multifunctional instrument of FIG. 5.
Figure 7:
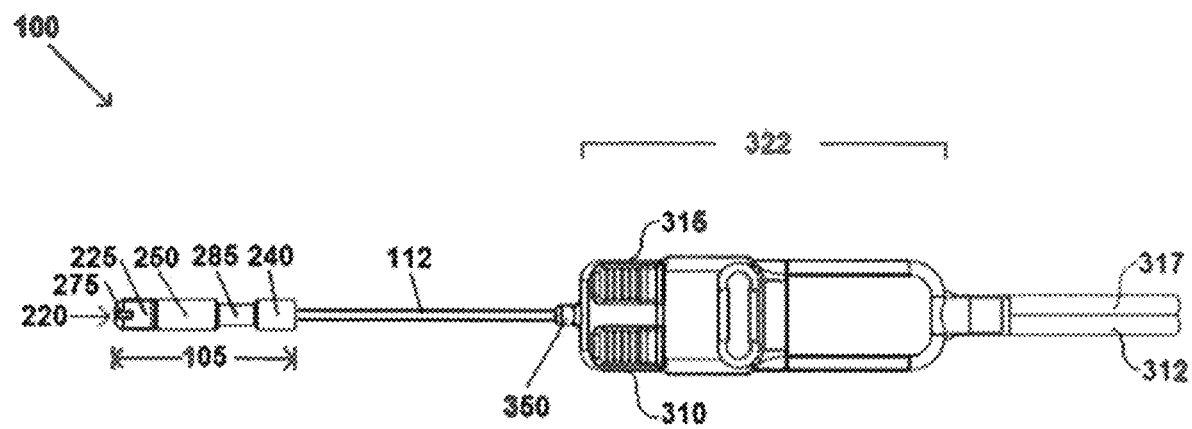
FIG. 7 is a top plan view of the multifunctional instrument of FIG. 5.
Figure 8:
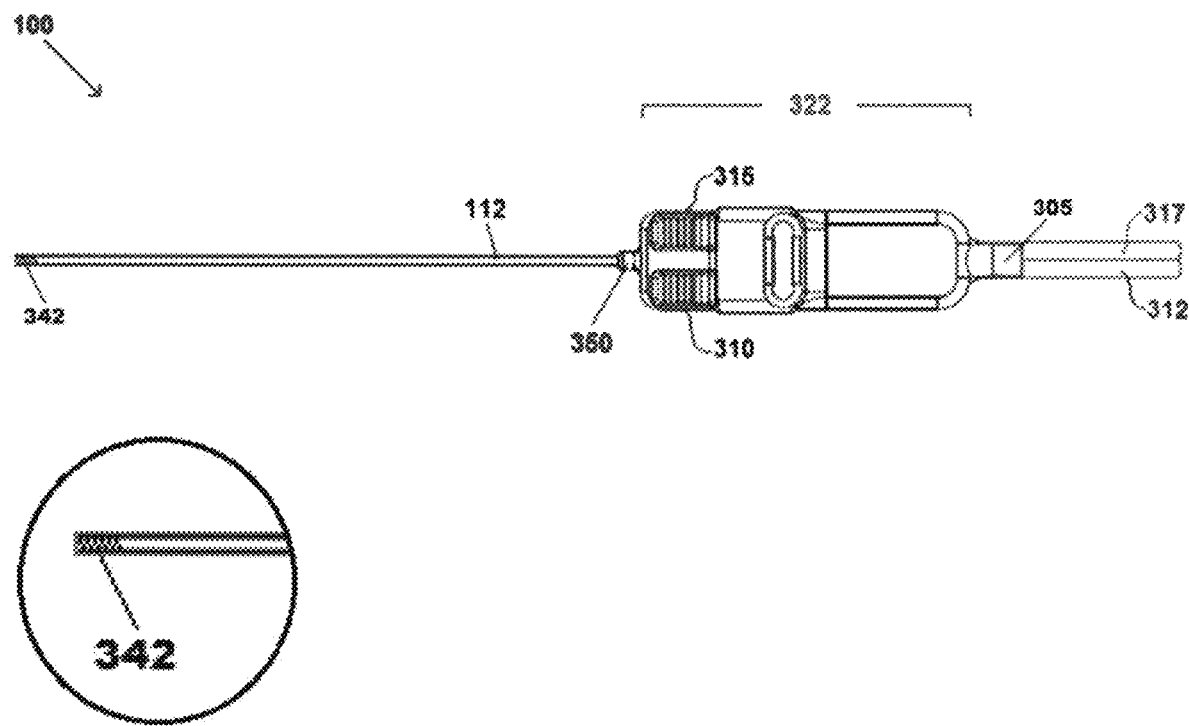
FIG. 8 is another top plan view of the multifunctional instrument of FIG. 5, showing a threaded tip.

As further shown in FIG. 5, the multifunctional instrument 100 may be part of an integrated system that includes a needlescopic instrument shaft 110 that has a piercing tip 340 that is utilized to perforate the percutaneous skin of a patient. With reference to FIG. 6, in an embodiment, the instrument shaft 110 with the piercing tip 340 may be just longer than a distance from the injection port 305 to the distal end of the tip of instrument shaft 112. This enables the instrument shaft 110 with the piercing tip to be inserted through the injection port and hollow body of the instrument shaft 112 such that the piercing tip 340 extends just beyond the threaded tip of the instrument shaft 112. In this manner, the piercing tip 340 of the shaft 110 may be utilized to pierce the skin so that the instrument shaft 112 can enter the body immediately thereafter, in a single step. That is, a single step may be utilized to both pierce the skin and insert the instrument shaft 112 into the body. Once the piercing is effected and the instrument shaft 112 is in position within the body cavity, the shaft 110 with piercing tip 240 can be removed from the instrument 100. Removal of the sharp tip is important to prevent inadvertent injury or perforation of intra-abdominal hollow organs.

Separately, the instrument head 105 may be introduced into the body cavity, e.g., a patient's abdomen, through a trocar and presented to the instrument shaft 112 for attachment thereto. In particular, once the instrument head 105 is delivered into the body cavity through a trocar, and the instrument shaft 112 is inserted into the body cavity, the distal end of the instrument shaft 112 can be attached to the instrument head 105 within the body by means of a threaded tip on the distal end of the instrument shaft 112, under continuous direct visualization via a laparoscope. In particular, the instrument shaft 112 is configured to attach to the instrument head 105 through the H-clip 270 by means of the threaded tip of the instrument shaft 112. The H-clip 270 allows the threaded tip to lock into the head with a simple push, but requires that the shaft be turned to unthread the tip for removal. Alternatively, the attachment housing 240 can include some other correspondingly threaded component for mating with the instrument shaft 112 to attach the instrument head 105 to the instrument shaft. Other attachment means are likewise possible without departing from the broader aspects of the present invention. Various suctioning, irrigating and cauterizing operations may then be performed within the body of a patient, as alluded to above. Importantly, utilizing this system and method, the instrument shaft 112 can be connected to the instrument head 105 within the body under continuous direct visualization through the introduction of the laparoscope through the trocar.

With particular respect to a cauterizing operation, rather than using the instrument head 105, another instrument shaft 113 having a spatula tip 345 may be connected to the body 322 of the multifunctional instrument 100 to establish electrical communication between a power supply and the spatula tip 345. The instrument shaft 113 may then similarly be inserted into the body cavity through the pathway used by the piercing tip 340 in order to provide for more precise and targeted cauterization of body tissues using spatula tip 345. Alternatively, the instrument shaft 113 with cauterizing tip 345 may be inserted through the injection port 305 so that the tip 345 protrudes from the distal tip of the instrument head 105 to provide precise cauterization of body tissues. In the preferred embodiment, the spatula tip 345, once inserted can be retracted a short distance into the instrument head with a sliding switch (not shown) or other similar actuating mechanism incorporated into the handle, such that the spatula tip 345 can be retracted or extended without removing the entire shaft. In such a mode, the device has a reduction in flow due to the presence of the spatula shaft inside the hollow instrument shaft, but allows for quicker deployment of the spatula tip 345 when needed.

It is contemplated that other instrument shafts having specialized tips may also be selectively connected to the body 322 of the multifunctional instrument 110, or inserted through the hollow passageway of the instrument shaft 112 via the injection port 305, to perform specialized operations and functions. The various shafts may have removable caps 306 for protecting the ends of the shafts. Moreover, instrument shaft 112 may be manufactured in various lengths so that a specific length shaft may be selected depending on the particular patient on which a surgical procedure is to be performed and/or the location of the surgical site within the body.

Figure 10:
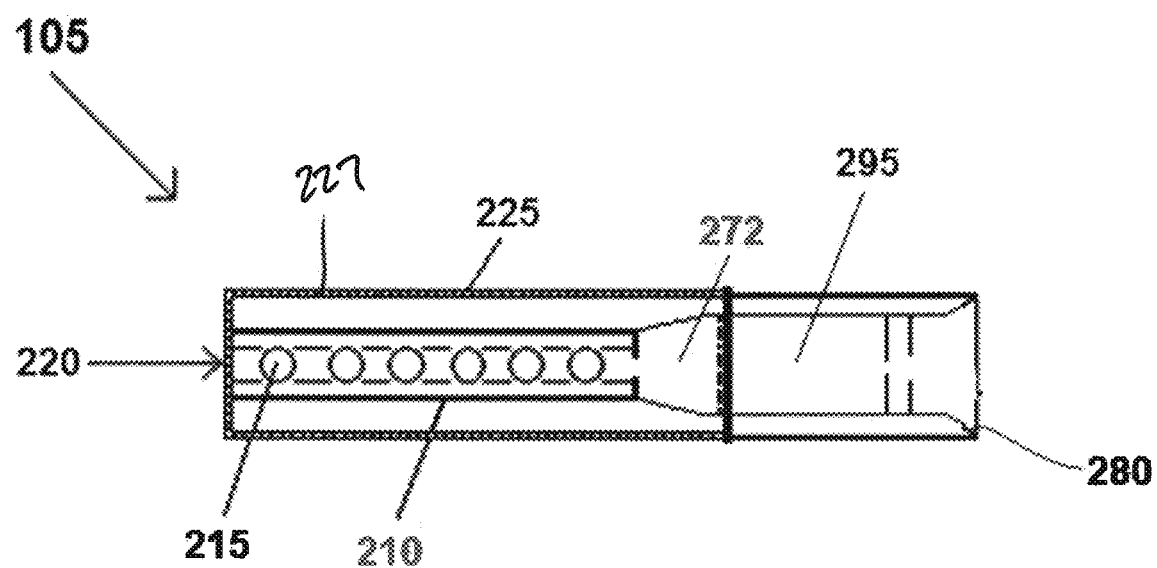
FIG. 10 is a cross-sectional view of another instrument head for a multifunctional instrument, according to alternative embodiment of the present invention.

Turning now to FIG. 10, in an embodiment, the cannula tube 210 and frame 225 may be surrounded by a gauze 227 or other material. The gauze 227 or other material may vary in composition, type and thickness.

Figure 11:
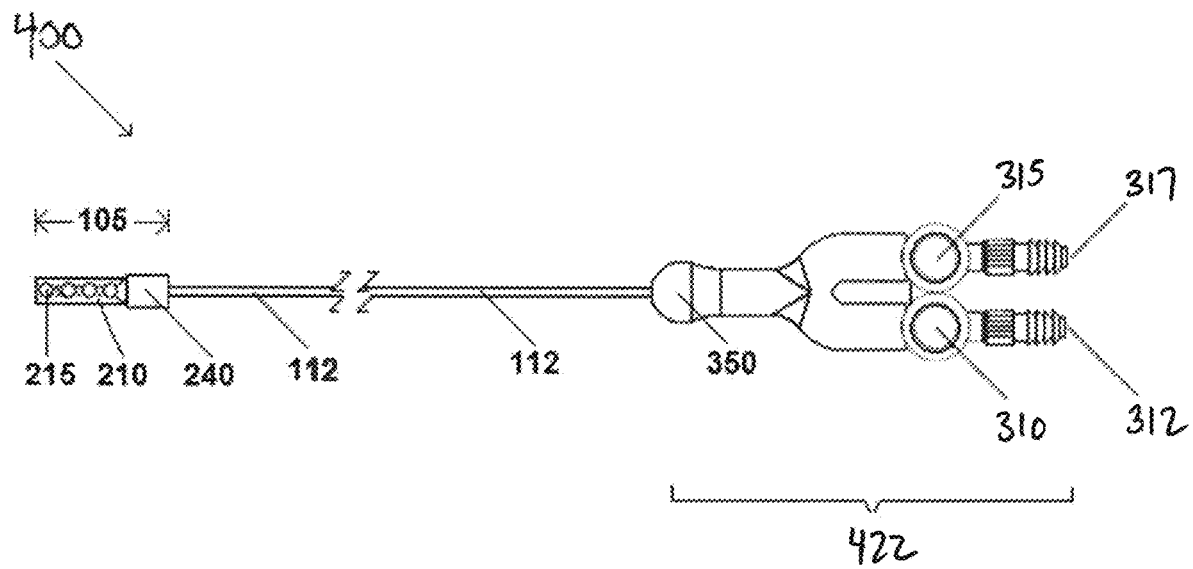
FIG. 11 is a perspective view of another multifunctional instrument, according to another embodiment of the invention.

With reference to FIG. 11, an alternative construction for a multifunctional instrument 400 according to another embodiment of the invention is shown. The multifunctional instrument is generally similar to the multifunctional instrument 100 described above, where like reference numerals indicate like parts. Rather than the body 322 being rectangular in shape, however, the body 422 of the multifunctional instrument 400 may be generally Y-shaped, and the vacuum tube 312 and the irrigation tube 317 may include hose barb or similar type fittings for connecting to a source of suction and irrigation fluid, respectively. The body may also be shaped in any manner typical of laparoscopic instrument handles, including a wand grip, gun grip, flute grip, or pencil grip.

Figure 12:
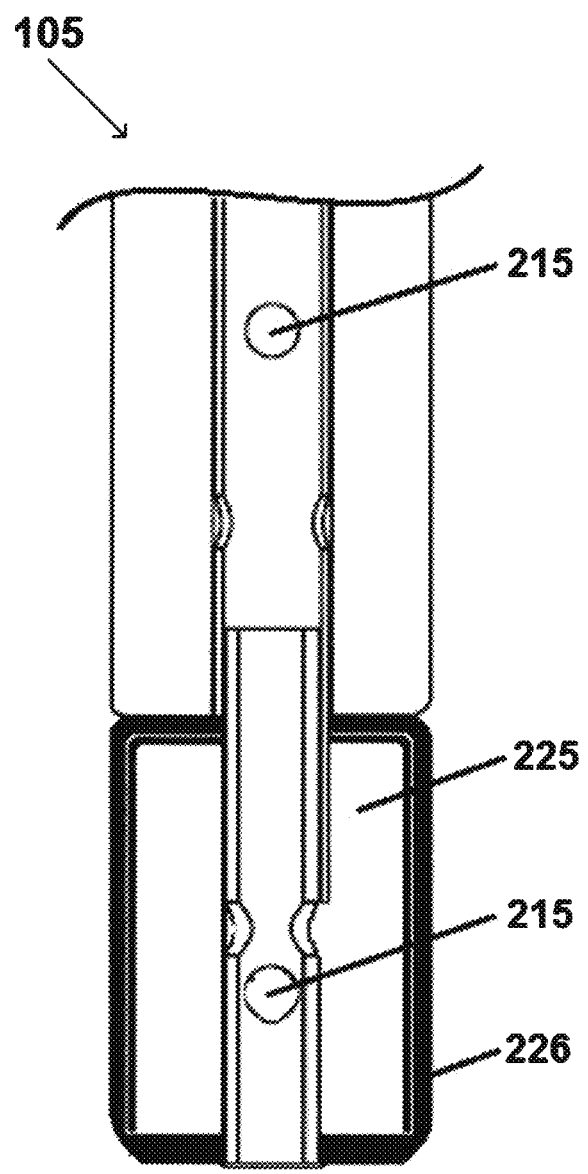
FIG. 12 is an enlarged, cross-sectional view of the instrument head of FIG. 10.

With respect to FIG. 12 the distal end of the instrument head 105 is illustrated showing how the distal end frame 225 may be wrapped with the covering material 226. These components are in union with each other by means of, but not limited to, applying an adhesive surface between them. The instrument head covering material 226 may be located at the distal tip of the instrument head 105 providing a smooth surface for the instrument head 105 to function in moving body tissues.

Figure 13:
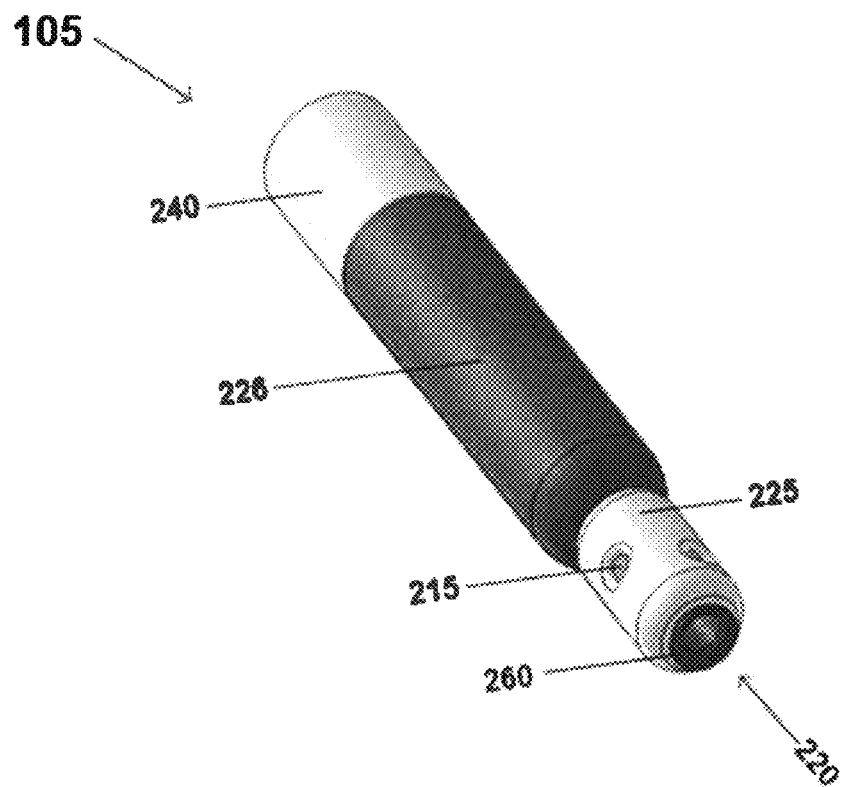
FIG. 13 is a perspective view of another instrument head for a multifunctional instrument, according to another embodiment of the present invention.

With respect to FIG. 13 a perspective view of an alternative embodiment of an instrument head 105 is illustrated. In this configuration, the attachment housing 240 is in union with the instrument head covering material 226 and distal end frame 225. A clear view of the cauterizing tip 260 is illustrated protruding just beyond the distal tip. The cauterizing tip 260 is not covered with any gauze like material, which would impede in its main function. In this illustration, the end frame 225 may have a gauze like material or other suitable covering material. In this embodiment, the orifices 215 are clearly exposed on the distal end of the instrument head 105 for maximum suction and or irrigation.

As discussed above, the present invention therefore provides a multifunctional instrument having an atraumatic/blunt tip/instrument head that can perform suction/irrigation, while also having the ability to perform the functions of a "peanut" dissector. The instrument head can be formed made of different materials over different regions, having the ability to perform different specialized functions. The instrument head is not limited to, but may be comprised of a single material or a combination of different materials optimized in some areas for absorption, other areas for the passage of suction and irrigation, and other areas for cleaning the laparoscope lens or cleaning other instruments' surfaces and jaws. Possible materials are not limited to, but may include, cotton, polyester, microfiber, or foam.

As discussed above, in certain embodiments, the multifunctional instrument is part of a system having, or otherwise is provided with, a detachable sharp inner piercing cannula or shaft. Its purpose is to provide a piercing edge used in penetrating the percutaneous skin. This process permits insertion of an elongated instrument shaft into the body cavity, allowing the instrument head to be attached inside the body through a specialized delivery system. This allows an extra-large head to be attached to a small diameter shaft to minimize incision size and eliminate the need for a trocar, but still provide the superior functionality of a full-sized head. The specialized delivery system may incorporate direct continuous visualization.

As discussed above, the instrument head is capable of performing a plurality of disparate functions. For example, the outer surface of the instrument head may be comprised of several different absorbent gauze materials located along the tip and side of the distal head. Another region on the head can act as a lens cleaner for the laparoscope, while other surfaces are used shaped and selected for absorption of fluids or other specialized function such as suction/irrigation pathways and smoke evacuation. The distal tip may be reinforced to provide superior dissection functionality. The distal end of instrument head may be embedded with a device called a mandrel that has a small orifice at the tip and several uniform openings or slots throughout its peripheral sides. The small orifices allow passage of liquids or gases used in the irrigation/evacuation process. Embedded in the head is an H-clip, or similar tight-fitting metal latch, that helps securely lock the instrument head to the instrument shaft. The design of such a feature allows the threaded tip of the instrument shaft to lock into place with a simple push, but be removed only with the turning of the threads. The absorbent material on the instrument head is preferably strong enough that it permits blunt dissecting of tissue materials, but soft enough that it permits absorption and irrigation of liquids.

As indicated above, the instrument head includes passageways/slots and orifices for irrigation, filtering layers for suction, and a specially designed core that provides a buffer space to maximize absorption and suction while minimizing clogging of the inner passageway. It can be covered in a single material or a combination of materials designed for absorption and dissection, such as foam, gauze, microfiber, cotton padding, and other commonly used materials. The width at different regions may be uniform or vary based on the function at each region of the head. There may be slits or other openings in the absorptive materials to allow for better suction. The distal tip may be hard plastic, covered in gauze, rubberized, or incorporate some combination. In some embodiments, the instrument shaft could be also used as a suction/irrigator even without the attached head. In some embodiments, the suction/irrigation pathway can be used to deliver hemostatic agents, including cryo agents such as CO2 gas and medicines, such as epinephrine or fibrin, via a 3-way port that allows easy introduction of such agents.

In another aspect of the invention, the instrument shaft may include a foot pad or other limiting device around the shaft, which would be able to selectively side up and down the portion of the shaft outside the body, and would be lockable into position in the case that the user is inserting the needle into the body, so that the distance it enters is limited and risk of injury is minimized. The feature would also allow the user to set the instrument at a particular depth to better retract or perform some other action that requires limited instrument movement. The foot could be a thin flat disk of 2-3 cm in diameter, or could be of any shape or size and could even incorporate an adhesive surface to better hold it into place. A pinching clip could also be incorporated at the handle or along the shaft to clip to the drapes and allow the surgeon to maintain the instrument in a particular orientation, typically to hold the handle down onto the drapes so the tip is firmly pressed into place to retract an organ.

The multifunctional instrument of the present invention also incorporates an electrocautery tip. The ability to cauterize tissue is important in most laparoscopic procedures, and necessary for certain types of dissection. The instrument head incorporates a metal tip at its most distal end and a standard electrocautery connector at the proximal end, with electrical communication between them through the shaft itself or a conductive element such as a wire or rod travelling through the center of the shaft. The shaft would need to be insulated for safety using a standard method of insulation such as a thin plastic sheathing. Standard grounding methods, such as placing an adhesive grounding pad on the patients back, would need to be used to protect the patient. The cautery would be activated with the use of a standard foot pedal, but could incorporate a button on the handle. The cautery tip could be the distal circular end of the shaft protruding beyond the gauze, potentially incorporating a feature that rounded and/or enlarged the end to improve tissue cautery. The tip could also be shaped in the typical cautery styles, such as a spatula, hook or needle, and can be made of any standard metal used for medical cautery, including memory metals capable of forming a specific shape upon deployment. The cautery tip may be incorporated into the head itself and/or introduced through the shaft by pushing a rod down along its length. The rod may be double ended, such that one end has a sharp tip for puncturing the skin to insert the instrument, and the other end has a cautery tip. In the embodiment where a cap is used on the rod, it may be removable and can switch from covering a cautery tip to covering the needle puncture tip after instrument insertion for safety purposes. In other embodiments, there are separate rods for the puncture and other various cautery tip styles. The cautery can be performed in the typical "dry" manner, or may be performed in combination with small controlled amounts of saline irrigation to achieve "saline-assisted" electrocautery, with has several benefits related to its lower temperature cautery. Being able to irrigate directly at the site of cautery provides this benefit, which is not available when using other cautery devices.

In another aspect of the invention, the multifunction device also acts as a smoke evacuator, using the suction function to evacuate plumes of smoke instead of evacuating liquid. Smoke generated during cauterizing or other uses of energy devices can be toxic to the patient and toxic to the surgeons, but often needs to be cleared out of the abdominal cavity to maintain clear visibility. Rather than evacuate this toxic gas into the air of the operating room, surgeons will often use a smoke evacuator device to actively or passively clean the smoke, often through filters. Unfortunately, problems exist limiting the usefulness of such devices. The ones that clear the air from the trocar cannot focus the extraction at the site of smoke generation, and are inefficient, potentially affecting the pressure in the abdomen. The use of suction devices with cannulas that can reach towards the site of cautery and remove the smoke as it is generated are more efficient and likely safer for the patient, but these devices take up a trocar that the surgeon often needs for other instruments and is therefore not used as frequently as it is needed. Because the present invention can remove smoke at the source when desired, and requires no trocar port, surgeons can have it ready when needed and simply keep it out of the way when not needed. Simply having it always present makes it a far superior smoke evacuator. In some embodiments, an in-line filter is provided that attaches in-line with the suction tubing, such that the smoke is filtered before it is pulled into the hospital's pipes and tubes. In other embodiment, the smoke is simply removed through the suction port and into the hospital's vacuum system directly. In some embodiments is can be pulled up to the abdominal wall, held in place, and the suction activated such that it clears the entire abdomen of smoke.

In an embodiment, the multifunctional instrument may be accompanied by an electronics module that senses the use of an energy device and automatically opens the suction valve such that smoke evacuation can automatically happen every time smoke is generated. The module may also have a feature that automatically stops smoke evacuation when the insufflation pressure gets too low.

The force of the irrigation spray can be strengthened with a pressure cuff around an IV bag of sterile fluid in the standard manner, or manually pumped, or generated in any way typically used in the operating room. Integrated into the previously mentioned electrics module or into a separate device is another module that senses the pressure on the fluid bag connected to the irritation tubing, and modulates it as needed. This would provide a constant irrigation pressure throughout the case without any constant maintenance by the staff. The cuff would also incorporate a feature to warm the irrigation fluid, since warmer fluid has been shown to benefit patients in numerous ways, including most importantly preventing hypothermia. The cuff may have a pouch for placing a disposable heating pack to keep the fluid warm, or could incorporate an electronic heating element in the embodiment where an electronic module is incorporated into the pressure cuff system.

The present invention therefore provides a multifunctional instrument having a thin shaft, on the order of 2 mm to 5 mm, and preferably less than 3 mm, to which a larger instrument head can be attached inside a body cavity. In one embodiment, the instrument shaft is less than approximately 2 mm in diameter. Accordingly, the multifunctional instrument of the present invention is capable of irrigation/suction, blunt dissection, smoke evacuation, electrocautery, lens cleaning, fluid delivery, or some subset combination of such functions, without having to make another large incision for the insertion of a trocar that results in scarring, discomfort and lengthy healing times.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A surgical instrument, comprising:
    an instrument shaft having a proximal end and a distal end having a threaded tip, and an interior passageway extending from the proximal end to the distal end, the interior passageway allowing for passage of fluid therethrough during a suction and/or irrigation operation;
    a housing connected to the proximal end of the instrument shaft;
    a first conduit disposed inside the housing and fluidly coupled to the instrument shaft, and being configured for selective connection to an irrigation source;
    a first switch configured to selectively control a flow of a fluid passing through the first conduit;
    a second conduit disposed inside the housing and fluidly coupled to the instrument shaft, and being configured for selective connection to a vacuum source;
    a second switch configured to selectively control a flow of a fluid passing through the second conduit;
    a third conduit disposed inside the housing and fluidly coupled to the instrument shaft;
    a piercing shaft configured for insertion through the third conduit for percutaneous insertion of the instrument shaft without the use of a trocar;
    a cauterization shaft configured for insertion through the third conduit for cauterization of tissue; and
    an instrument head having a proximal end and a distal end, an outer housing, and an inner cannula tube within the outer housing and defining an interior passageway, the proximal end having a clip having an H-shaped opening configured to receive the threaded tip of the instrument shaft for removably connecting the instrument head to the distal end of the instrument shaft, and the distal end of the instrument head having an axial opening in fluid communication with the interior passageway of the instrument head;
    wherein the instrument head includes a cauterizing tip located on the distal end of the instrument head adjacent to the opening;
    wherein the instrument shaft is conductive such that when the instrument head is connected to the instrument shaft, the instrument shaft is in electrical communication with the instrument head and the cauterizing tip and the instrument shaft forms a conductive pathway between the cauterizing tip of the instrument head and power source to deliver electrical energy from the power source, through a wall of the instrument shaft, to the cauterizing tip during a cauterization operation;
    wherein the surgical instrument is operable in a first cauterization mode whereby the cauterizing tip of the instrument head is used to cauterize tissue using the instrument head;
    wherein the surgical instrument is operable in a second cauterization mode whereby a tip of the cauterization shaft inserted through the third conduit and the instrument head is used to more precisely cauterize tissue using the cauterization shaft;
    wherein the instrument shaft serves both as a conduit for the passage of fluid during suction and/or irrigation functions and as a conductive pathway to provide the electrical energy from the power source to the cauterizing tip of the instrument head;
    wherein the inner cannula tube of the instrument head includes a plurality of radial orifices located along a longitudinal extent of the inner cannula tube and providing fluid communication with the interior passageway defined by the inner cannula tube; and
    wherein the outer housing, at the distal end, includes a plurality of longitudinal slots in fluid communication with at least one of the radial orifices in the inner cannula tube.

2. The surgical instrument of claim 1, further comprising:
    a cable conductively coupled to the instrument shaft and being configured for selective electrical connection to a power source.

3. The surgical instrument of claim 1, wherein:
    the instrument shaft is less than 3 millimeters in diameter.

4. The surgical instrument of claim 1, wherein:
    the housing contains at least a portion of the first conduit, the second conduit, the third conduit and the cable.

5. The surgical instrument of claim 1, further comprising:
    the piercing shaft removably received within the interior passageway of the instrument shaft, the piercing shaft including a piercing tip configured to pierce skin of a patient to create an opening for near simultaneous insertion of the instrument shaft;
    wherein the piercing shaft is configured such that the piercing tip protrudes beyond the distal end of the instrument shaft when received within the interior passageway of the instrument shaft.

6. The surgical instrument of claim 1, further comprising:
an injection port formed in the body at a proximal end of the third conduit and in fluid communication with the third conduit;
wherein the injection port allows for the introduction of a fluid through the third conduit and the instrument shaft.

7. The surgical instrument of claim 1, further comprising:
at least one absorbent surface on a periphery of the instrument head, the absorbent surface providing a cleaning surface for a medical device.

8. The surgical instrument of claim 7, wherein:
the at least one absorbent surface is at least two absorbent surfaces, wherein at least one of the absorbent surfaces comprises a different material from another one of the absorbent surfaces.

9. The surgical instrument of claim 1, wherein:
the first, second, and third conduits are substantially parallel to each other; and
the third conduit is disposed horizontally between the first conduit and the second conduit.

10. The surgical instrument of claim 1, wherein the surgical instrument further comprising:
a connector port disposed inside the housing; the connector port is in fluid communication with the first conduit and the second conduit;
wherein the connector port comprising an outlet port in fluid communication with the instrument shaft.

11. The surgical instrument of claim 10, wherein:
the connector port comprising a shaft channel receiving the piercing shaft or the cauterization shaft, permitting the piercing shaft or the cauterization shaft passing therethrough and received by the instrument shaft.

12. The surgical instrument of claim 1, wherein:
the cauterization shaft is slidably received within the third conduit and selectively moveable between a cauterization position where a spatula tip of the cauterization shaft protrudes beyond the distal end of the instrument head, and a retracted position where the spatula tip is housed within the instrument head; and
wherein the surgical instrument further includes an actuator associated with the housing and operatively connected to the cauterization shaft for selectively moving the cauterization shaft between the cauterization position and the retracted position.

13. The surgical instrument of claim 1, wherein:
the cauterizing tip is annular and surrounds the axial opening.

14. The surgical instrument of claim 1, wherein:
the cauterizing shaft is selectively extendable beyond the distal end of the instrument head, and retractable within the instrument head, via an actuating mechanism of the surgical instrument, so that a cauterizing tip of the cauterizing shaft can be selectively retracted without removing the entire cauterizing shaft from the instrument shaft.

15. The surgical instrument of claim 1, wherein:
the instrument head includes:
a first cylindrical portion having an attachment housing having a conical recess for receiving the distal end of the instrument shaft, the first cylindrical portion being located at the proximal end of the instrument head;
a second cylindrical portion having a reduced diameter relative to a diameter of the first cylindrical portion, the second cylindrical portion being located adjacent to the first cylindrical portion, the second cylindrical portion having an exterior surface of a material configured for cleaning a lens of a laparoscope;
a third cylindrical portion adjacent to the second cylindrical portion, the third cylindrical portion having a diameter that is greater than the diameter of the second cylindrical portion, the third cylindrical portion having a covering material including at least one of a gauze, foam or microfiber material; and
a rounded, atraumatic tip at the distal end of the instrument head adjacent to the third cylindrical portion, the rounded, atraumatic tip having the plurality of longitudinal slots in fluid communication with the interior passageway of the inner cannula tube, the plurality of longitudinal slots extending at least partially into an axial face of the instrument head at the distal end.

16. A surgical instrument, comprising:
an electrically-conductive instrument shaft having a proximal end and a distal end having a threaded tip, and an interior passageway extending from the proximal end to the distal end, the interior passageway allowing for passage of fluid therethrough during a suction and/or irrigation operation;
an instrument head having a proximal end and a distal end, and outer housing, and an inner cannula tube defining an interior passageway, the proximal end having a clip having an opening configured to receiving the threaded tip of the instrument shaft for removably connecting the instrument head to the distal end of the instrument shaft, and the distal end of the instrument head having an opening in fluid communication with the interior passageway of the instrument head, the connection means and the attachment means defining a releasable connection;
wherein the instrument head includes a cauterizing tip located on the distal end of the instrument head adjacent to the opening;
wherein when the instrument head is connected to the instrument shaft, the instrument shaft, itself, forms an electrically conductive pathway between the cauterizing tip of the instrument head and a power source to deliver electrical energy from the power source, through the instrument shaft, to the cauterizing tip of the instrument head during a cauterization operation; and
a cauterization shaft configured for insertion through the instrument shaft for cauterization of tissue using a tip of the cauterization shaft;
wherein the surgical instrument is operable in a first cauterization mode whereby the cauterizing tip of the instrument head is used to cauterize tissue using the instrument head;
wherein the surgical instrument is operable in a second cauterization mode whereby the tip of the cauterization shaft inserted through the instrument shaft and the instrument head is used to more precisely cauterize tissue using the tip of the cauterization shaft;
wherein the instrument shaft serves both as a conduit for the passage of fluid during suction and/or irrigation functions and as an electrically conductive pathway to provide the electrical energy from the power source to the cauterizing tip of the instrument head;
wherein when the instrument head is connected to the instrument shaft, the cauterizing tip of the instrument head is in electrical communication with the power source through the electrically-conductive instrument shaft such that electrical energy can be transmitted from the power source, through the electrically conductive-instrument head, through the releasable connection between the instrument shaft and the instrument head, and to the cauterizing tip;

wherein the inner cannula tube of the instrument head includes a plurality of radial orifices located along a longitudinal extent of the inner cannula tube and providing fluid communication with the interior passageway defined by the inner cannula tube;

wherein the outer housing, at the distal end, includes a plurality of longitudinal slots in fluid communication with at least one of the radial orifices in the inner cannula tube; and wherein the proximal end of the instrument head includes a conical surface adjacent to the inner cannula tube for facilitating connection of the instrument shaft to the instrument head.

17. The surgical instrument of claim 16, wherein:

the cauterizing shaft is selectively extendable beyond the distal end of the instrument head, and retractable within the instrument head, via an actuating mechanism of the surgical instrument, so that the tip of the cauterizing shaft can be selectively retracted without removing the entire cauterizing shaft from the instrument shaft.

18. A surgical instrument, comprising:

an instrument shaft having a proximal end and a distal end, and an interior passageway extending from the proximal end to the distal end, the interior passageway allowing for passage of fluid therethrough during a suction and / or irrigation operation; and an instrument head configured for releasable connection to the distal end of the instrument shaft, the instrument head including:
 a proximal end;
 a distal end;
 an inner cannula tube defining an interior passageway;
 an opening at the distal end;
 a cauterizing tip adjacent to the opening;
 a first cylindrical portion having an attachment housing having a conical recess for receiving the distal end of the instrument shaft, the first cylindrical portion being located at the proximal end of the instrument head;
 a second cylindrical portion having a reduced diameter relative to a diameter of the first cylindrical portion, the second cylindrical portion being located adjacent to the first cylindrical portion, the second cylindrical portion having an exterior surface of a material configured for cleaning a lens of a laparoscope;
 a third cylindrical portion adjacent to the second cylindrical portion, the third cylindrical portion having a diameter that is greater than the diameter of the second cylindrical portion, the third cylindrical portion having a covering material including at least one of a gauze, foam or microfiber material; and
 a rounded, atraumatic tip at the distal end of the instrument head adjacent to the third cylindrical portion, the rounded, atraumatic tip having a plurality of slots in fluid communication with the interior passageway of the inner cannula tube and extending at least partially into an axial face of the instrument head at the distal end.

\* \* \* \* \*